United States Patent [19]

Stonehart et al.

[11] Patent Number: 5,523,181
[45] Date of Patent: Jun. 4, 1996

[54] POLYMER SOLID-ELECTROLYTE COMPOSITION AND ELECTROCHEMICAL CELL USING THE COMPOSITION

[75] Inventors: Paul Stonehart, Madison, Conn.;
Masahiro Watanabe, 2412-8,
Wadamachi, Kofu-shi, Yamanashi, Japan

[73] Assignees: Masahiro Watanabe, Japan; Stonehart Associates, Inc., Madison, Conn.

[21] Appl. No.: 126,337

[22] Filed: Sep. 24, 1993

[30] Foreign Application Priority Data

Sep. 25, 1992 [JP] Japan .................................. 4-256804
Sep. 25, 1992 [JP] Japan .................................. 4-256805

[51] Int. Cl.$^6$ ................................................ H01M 10/40
[52] U.S. Cl. .......................... 429/192; 429/193; 204/296
[58] Field of Search ........................... 204/296; 429/192, 429/193

[56] References Cited

U.S. PATENT DOCUMENTS 3,616,319 10/1971 Johnson et al. ............... 204/296 X
3,920,534 11/1975 Jensen et al. ................... 204/296 X
4,289,601 9/1981 Kadija ................................. 204/296
4,990,413 2/1991 Lee et al. .......................... 429/193 X

FOREIGN PATENT DOCUMENTS 60-51502  3/1985  Japan .

*Primary Examiner*—Stephen Kalafut
*Attorney, Agent, or Firm*—Klauber & Jackson

[57] ABSTRACT

The polymer solid-electrolyte composition according to the present invention comprises a polymer solid electrolyte selected from the group consisting of perfluorocarbon sulfonic acid, polysulfones, perfluorocarbonic acid, styrene-divinylbenzene sulfonic acid cation-exchange resins and styrene-butadiene anion-exchange resins, and 0.01–50% by weight of fine particle silica and/or fibrous silica fiber relative to the weight of the polymer solid electrolyte.

6 Claims, 3 Drawing Sheets

POLYMER SOLID-ELECTROLYTE COMPOSITION AND ELECTROCHEMICAL CELL USING THE COMPOSITION

BACKGROUND OF THE INVENTION

1. Field of the Invention

The present invention relates to a polymer solid-electrolyte composition having improved ion conductivity, and to an improvement of an electrochemical cell using it.

2. Description of the Background Art

It is known that perfluorocarbon sulfonic acid, polysulfones, perfluorcarbonic acid, styrene-divinylbenzene sulfonic acid cation-exchange resins and styrene-butadiene anion-exchange resins are available as conventional polymer solid electrolytes. Particularly, perfluorocarbon sulfonic acid, a fluorinated resin developed by DuPont and known under the trade name of NAFION®, is noted as a polymer solid electrolyte which is excellent in chemical stability and heat resistance. NAFION® comprises the base of the copolymer of tetrafluoroethylene and perfluorovinyl ether, on which some sulfonate groups are present as ion-exchange functional groups.

Among them, the granular polymer solid electrolyte is packed in a column and the like, and used for the purification of water and others. A membrane, in which a polymer solid electrolyte is prepared in the form of film has been used as an ion-exchange membrane type of oxygen sensor and an ion-exchange membrane of electrochemical cells such as the salt-electrolysis and water-electrolysis cells, besides the fuel cell. A study has also been carried out to determine whether the membrane can be used as the ion-exchange membrane in an ion-exchange membrane cell for acetaldehyde synthesis. Among these electrochemical cells, particularly the fuel cell, which converts directly chemical energy from hydrogen, reformed natural gas, and the like to electrical energy, generates cleaner energy and has higher efficacy of power generation compared with other generators such as an internal combustion engine, a gas turbine or a diesel engine; and therefore it is noted to use as power source for an electric vehicle, a space craft and the like.

The above-mentioned electrochemical cells are briefly described as follows. The fuel cell converts chemical energy into electrical energy; the ion-exchange membrane type of oxygen sensor and the like measures the amount of a substance into information; and the water electrolysis cell and the like converts electrical energy into chemical energy. In all cases, the donation-acceptance reaction of electrons on an anode or cathode electrode produces an ionic current flow in the polymer solid-electrolyte membrane (in the ion-exchange membrane). This ionic current is produced by the movement of cations or anions from an anode to a cathode, or that of cations or anions from a cathode to an anode. Since this movement of ions is carried out through ion-exchange functional groups such as sulfonic acid, amine or carboxyl groups, the higher the ion-exchange functional group content becomes, the smaller the electrical resistance, i.e., the specific resistance will be less. If water occupies the space between the ion-exchange functional groups, the water molecules are thought to move. When polymer solid electrolytes are dried, their ion conductivity tends to decrease markedly. Therefore, better moisture absorption of a polymer solid electrolyte prevents its ion conductivity from decreasing. This maintenance of ion conductivity makes the energy loss smaller when a current flows in the polymer solid electrolyte, then a high-performance electrochemical cell can be obtained. The membrane where moisture is sufficiently absorbed also prevents the reaction gases from passing through the membrane directly.

Thus, in order to obtain a high-performance electrochemical cell, it is required to improve the ion conductivity by increasing the water content of the polymer solid electrolyte as well as by lowering the specific resistance thereof. Hitherto, improvement methods have been proposed as follows:

1) The method for improving the ion conductivity of the polymer solid-electrolyte membrane by increasing the level of ion-exchange functional groups in polymer solid electrolytes including hydrocarbon ion-exchange resins, fluorinated resins such as NAFION® (the trade name of perfluorocarbon sulfonic acid developed by DuPont in the U.S.A.), and the like so as to lower the specific resistance of the polymer solid-electrolyte membrane.

2) The method for improving the ion conductivity of the polymer solid-electrolyte membrane by mechanically processing the membrane prepared with the polymer solid electrolytes to make the membrane thinner so as to lower the resistance of the polymer solid electrolyte membrane.

3) The method for improving the ion conductivity of the polymer solid-electrolyte membrane by putting moisture-transportive fibers in the form of twisted yarn to moisten the polymer solid-electrolyte membrane through the fibers, thereby making the moisture absorption of the membrane improve by increasing the water content of the polymer solid-electrolyte membrane.

4) The method for improving the ion conductivity of the polymer solid-electrolyte membrane by moistening the reaction gas at the anode side or cathode side with water vapor or water droplets so as to make the membrane moisten indirectly, as in the case of an electrochemical cell as well as a fuel cell to which the reaction gas is supplied.

If the number of the ion-exchange functional groups in the polymer solid electrolytes is increased, the mechanical characteristic of the polymer is lost in the cases of the hydrocarbon ion-exchange resins; and thus there arises a problem that it is difficult to produce the electrochemical cells because the polymer solid-electrolyte membrane is not easily joined to the anode or cathode. Further, as the fluorinated membranes such as NAFION® and the like become fluidized, it is difficult technically to introduce a number of ion-exchange functional groups.

On the other hand, if the thickness of the polymer solid-electrolyte membrane is made smaller, the membrane itself has low mechanical strength; and therefore the polymer solid-electrolyte membrane is easily damaged.

Furthermore, the membrane can be moistened by the method in which fibers in the form of twisted yarn, are placed into the membrane, but the increased membrane thickness due to the thickness of the sandwiched fibers leads to a decrease of the ion conductivity.

Furthermore, the method in which the reaction gas is moistened with water vapor or water droplets brings about a decrease in the partial pressure of the reaction gas because the partial presure of the reaction gas is diluted by the water vapor content, and this results in a factor that decreases the electrochemical cells' performance due to dilution of the reaction gas in the catalyst layer. Since it is difficult to vary the amount of water vapor required by the membrane depending on the fluctuating load, insufficient supply with water makes the membrane dry, or on the contrary, excess supply with water makes the catalyst layer too wet. As a result, the cell's performance is degraded.

Consequently, it is necessary to develop polymer solid electrolytes having improved ion conductivity which increase the electrochemical cells' performance since membranes prepared with conventional polymer solid electrolytes have difficulties when used as ion-exchange membranes in operating cells.

SUMMARY OF THE INVENTION

Accordingly, an object of the present invention is to provide a polymer solid-electrolyte composition in which the polymer solid electrolyte has an increased water content and improved ion conductivity as well as decreased specific resistance, and an electrochemical cell using the composition.

According to the first aspect of the present invention, there is provided the most preferable polymer solid-electrolyte composition available for the membrane of the electrochemical cell, the composition comprising a polymer solid electrolyte selected from the group consisting of perfluorocarbon sulfonic acid polysulfones, perfluorocarbonic acid, styrene-divinylbenzene sulfonic acid cation-exchange resins and styrene-butadiene anion-exchange resins, and 0.01–50% by weight of fine particle silica and/or fibrous silica fiber relative to the weight of the polymer solid electrolyte.

According to the second aspect of the present invention, there is provided an electrochemical cell having improved performance, the cell consisting of an anode, a polymer solid-electrolyte layer and a cathode in which a composition comprising a polymer solid electrolyte selected from the group consisting of perfluorocarbon sulfonic acid, polysulfones, perfluorocarbonic acid, styrene-divinylbenzene sulfonic acid cation-exchange resins and styrene-butadiene anion-exchange resins, and 0.01–50% by weight of fine particle silica and/or fibrous silica fiber relative to the weight of the polymer solid electrolyte is used as at least one of the electrolyte in the anode and/or the cathode, or the polymer solid-electrolyte layer.

According to the third aspect of the present invention, there is provided an polymer solid-electrolyte type of fuel cell having improved performance, the polymer solid-electrolyte type of fuel cell which has a cathode current collector, a cathode catalyst layer, a polymer solid-electrolyte layer, an anode catalyst layer and an anode current collector laminate, the cathode catalyst layer supplied with an oxidative gas and the anode catalyst layer supplied with a fuel gas in which at least one of the polymer solid-electrolyte layer, the cathode layer and the anode layer contains fine particle silica and/or fibrous silica fiber.

As a result of intensive research to obtain methods by which the ion conductivity of polymer solid electrolytes is improved, the present inventors surprisingly have found that a composition comprising a polymer solid electrolyte selected from the group consisting of perfluorocarbon sulfonic acid, polysulfones, perfluorocarbonic acid, styrene-divinylbenzene sulfonic acid cation-exchange resins and styrene-butadiene anion-exchange resins has the smaller specific resistance and larger water content so as to markedly improve the ion conductivity to achieve the present invention.

The fine particles of silica having large specific surface area seem to provide a high moisture absorption. This finding suggests that the polymer solid-electrolyte composition containing silica and/or silica fiber may have a lower specific resistance and improved ion conductivity due to increased water content.

Further, it is found that by making the silica and/or silica fiber containing polymer solid-electrolyte composite, the membrane is able to have a larger water-retentive quantity to prevent the ion conductivity from decreasing. Direct permeation of the reaction gases across the cell is also inhibited.

Moreover, in the case of making membranes and electrodes containing silica fiber, the preparation of membranes with the polymer solid-electrolyte composition is able to show increased mechanical strength, so the preparation of thinner membranes can improve the cell conductivity.

The silica according to the present invention is preferably a high pure silica in an amorphous crystalline structure which has a fine particle size and a high specific surface area. The fine particle size is important not only to maintain the high specific surface area but also to make the polymer solid-electrolyte contain the silica evenly. Moreover, in the same particle sizes, the higher the surface area, that is, more porous, the higher the hygroscopicity, so that the specific resistance of the polymer solid-electrolyte composition is reduced. To be concrete, a mean primary particle size is 0.1 μm or less, preferably 0.01 μm or less. The surface area in the BET measuring method is 27 $m^2/g$ or more, preferably 130 $m^2/g$ or more.

The silica fiber according to the present invention has a diameter of 6 μm or less and a surface area of 0.3 $m^2/g$ or more by the BET measuring method. With the desired silica fiber content at 0.01–50% by weight, preferably 0.1–20% by weight relative to the weight of the polymer solid electrolyte, good ionic conductivity is obtained.

Examples of some suitable fine particle silicas are: Aerosil 380® from Nippon Aerosil; Cab-O-Sil® Garde EH-5 from Cabot Corp. (Tuscola, Ill.); and Snowtex-O® (a dispersion of silica in water) from Nissan Chemical Industries, Ltd.

Furthermore, in the cases that fine particle silica and/or fibrous silica fiber are to be contained in the polymer solid electrolyte, the silica and/or the silica fiber and the polymer solid electrolyte is suspended or dispersed in hydrophilic solvents such as methanol, ethanol, isopropanol, or butanol, and then the suspensions or solutions are mixed. As a result, the specific resistance of the resulting ion-exchange membranes is preferably decreased.

Examples of the polymer solid electrolytes which contain the above-mentioned silica and/or silica fiber include perfluorocarbon sulfonic acid, polysulfones, perfluorocarbonic acid, styrene-divinylbenzene sulfonic acid cation-exchange resins and styrene-butadiene anion-exchange resins, as mentioned above. Particularly, perfluorocarbon sulfonic acid (the trade name: NAFION®) is preferably used because it is excellent in chemical stability and heat resistance.

One of the methods for preparing the polymer solid-electrolyte compositions of the present invention will be illustrated by the example using the fine particle silica. First, a solution of 5% by weight of the above-mentioned polymer solid electrolyte in isopropanol is mixed with a dispersion of 0.01–50% by weight of silica (e.g., Aerosil 380® under the trade name available from Nippon Aerosil Co., Ltd.; the mean primary particle size, 0.007 μm) in isopropanol (concentration: 5 g/l) and mixed with a ultrasonic homogenizer. Subsequently, the resulting solution is poured into a membrane-molding vessel and dried under a reduced pressure at 60° C. to remove isopropanol so as to prepare the membrane. The prepared membrane is hydrolyzed to form the desired ion-exchange functional group. The membrane preparation also can be performed by an extrusion molding or screen process printing technique, or any other membrane making process.

An example where the above-mentioned fine particle silica and/or silica fiber is contained in a polymer solid electrolyte include a method in which, following the membrane preparation, the resulting membrane is coated with the above-mention silica and/or silica fiber on the membrane surface directly, and subsequently the silica and/or silica fiber is embedded into the surface layer by heating or a contact-bonding treatment such as hot pressing and the like. In this case, the silica and/or silica fiber content on the surface of the polymer solid-electrolyte membrane is adjusted to 0.01–50% by weight.

As described above, the polymer solid-electrolyte/silica composition of the present invention, which has small specific resistance and high moisture absorption, is useful for applications in ion-exchange membrane type of oxygen sensors, salt-electrolysis or water-electrolysis cells by the ion-exchange membrane method, and ion-exchange membrane type of acetaldehyde synthesis, in addition to fuel cells. When the polymer solid-electrolyte/silica composition is used as a polymer solid-electrolyte layer in the electrochemical cell consisting of an anode, polymer solid-electrolyte layer and cathode, it is desired that the composition is prepared so as to be a film having a thickness of about 0.03–0.2 mm, preferably 0.05–0.1 mm. The thinner the membrane, the better the ion conductivity.

Among electrochemical cells, an electrochemical cell which has bonded catalyst layers as the anode and cathode with the polymer solid electrolyte type of fuel cell in able to use not only the polymer solid-electrolyte compositions of the present invention as a polymer solid-electrolyte layer, but also the silica with the catalyst particles in the catalyst layer, which are coated by the polymer solid-electrolyte compositions in the form of a film. Then, in the case of the polymer solid electrolyte type of fuel cell, the silica and/or silica fiber content in the cathode catalyst layer and anode catalyst layer are shown. To promote the electrode reaction in the catalyst layer, it is desired that the weight ratio of the catalyst particle (or the catalyst in which platinum is used and dispersed on the surface of carbon particles) to the polymer solid electrolyte is allowed to be from 1/9 to 5/5. As described above, when the silica content is in the range of 0.01–50% by weight relative to the polymer solid electrolyte, the specific resistance is decreased and water content of the catalyst layer is increased. It is preferable that 0.0006–31% by weight of silica relative to the catalyst layer is provided.

In the case with the catalyst particle (or the catalyst in which platinum was dispersed on the surface of carbon particles), the polymer solid electrolyte, and silica and/or silica fiber is suspended or dispersed in hydrophilic solvents such as methanol, ethanol, isopropanol, or butanol, and then the suspension or solution is mixed as described for the polymer solid-electrolyte layer. As a result, the specific resistance of catalyst layers is preferably decreased. As also described above, providing the silica and/or silica fiber in the cathode catalyst layer for a fuel cell prevents water generated by the electrode reaction on the cathode catalyst layer from vaporizing into the gas phase. Water can be retained in the cell system when generation of water by the cell is decreased as in the case of the discontinuation of cell operation or of decreased power generation. Excess water produced at the cathode is transported to the anode side to be the water source for the polymer solid-electrolyte layer anode (when the anode and polymer solid-electrolyte is easily dried) as is the case at high power generation in fuel cells. Placing the silica and/or silica fiber contained in the anode catalyst layer further prevents the anode from drying and promotes reverse transport of water from the cathode side to the anode side.

As described above, among the electrochemical cells having catalyst layers in the anode and cathode, including the polymer solid-electrolyte layer type of fuel cell, even a cell in which silica and/or silica fiber is contained in only one layer out of the polymer solid electrolyte, cathode catalyst layer, or anode catalyst layer can improve the cell performance due to the respective effect. It is preferred that the silica and/or silica fiber is contained in at least the polymer solid-electrolyte layer. Further, by providing the silica and/or silica fiber in all of the polymer solid-electrolyte layer, cathode catalyst layer and anode catalyst layer, the cell performance can be improved, and operated under non-humidifying conditions. That is, placing the silica in the cathode catalyst layer when water is generated prevents the water from the cathode catalyst layer from vaporizing excessively in the reaction gas, and promotes the migration of excess water from the cathode catalyst layer to the polymer solid-electrolyte layer and then to the anode catalyst layer. Therefore, since water in the closed system moves and migrates across the cell, the electrochemical cell can be operated without external humidifying conditions. In addition, the respective silica and/or silica fiber content in the polymer solid-electrolyte layer. cathode catalyst layer and anode catalyst layer is preferably varied in proportion to the movement and diffusion in the range of the above-mentioned contents. For example, higher silica and/or silica fiber content may be contained at the anode catalyst layer side which is more easily dried, whereas smaller silica and/or silica fiber content may be contained in the cathode catalyst layer side. On the other hand, the silica and/or silica fiber, which is coated on at least one surface of the contact surfaces of the anode catalyst layer and the polymer solid-electrolyte layer, may be embedded into the surface layer by heating and contact-bonding treatment such as the hot pressing and the like. Similarly, the silica and/or silica fiber, which is coated on the contact surface of the anode catalyst layer and anode current collector, that of the polymer solid-electrolyte layer and cathode catalyst layer, and that of the cathode catalyst layer and cathode current collector, may also be embedded. In these cases, the silica and/or silica fiber content is preferably adjusted to 0.0006–31% by weight.

The polymer solid-electrolyte/silica composition of the present invention, in which the fine particle silica having a mean primary particle size of 0.1 µm or less and/or fibrous silica fiber having a diameter of 6 µm or less relative to the weight of the above-mentioned polymer solid electrolyte are contained, can decrease the specific resistance of the polymer solid-electrolyte compositions.

When used as an electrolyte in an electrochemical cell consisting of an anode, polymer solid-electrolyte layer and cathode, or as a polymer solid-electrolyte layer the above-mentioned polymer solid-electrolyte/silica compositions are used for one or more of them, the electrochemical cells having better performance can be prepared.

As described above, the polymer solid-electrolyte composition comprises 0.01–50% by weight of the fine particle silica (mean primary particle size of 0.1 µm or less) and/or fibrous silica fiber (diameter of 6 µm or less) relative to the weight of the polymer solid electrolyte; and thus it will be a more useful composition having improved ion conductivity compared with the same polymer solid electrolyte without the silica.

Therefore, when as an electrolyte contained in anode and/or cathode of the electrochemical cell consisting of an anode, polymer solid-electrolyte layer and cathode, or as a polymer solid-electrolyte layer the above-mentioned polymer solid-electrolyte compositions are used for one or more of them, the electrochemical cells having better performance can be prepared. In the electrochemical cells, for example in the polymer solid-electrolyte membrane type of fuel cell, if the fine particle silica and/or fibrous silica fiber are contained in all of the ion-exchange membrane, cathode catalyst layer and anode catalyst layer, the cell can be operated without humidification.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein.

DETAILED DESCRIPTION OF THE INVENTION AND PREFERRED EMBODIMENTS

A detailed description will follow of the preferred embodiment of Polymer Solid-electrolyte Composition and Electrochemical Cell using the Composition to the present invention with reference to the accompanying drawings.

EXAMPLE 1

The silica content, water content and specific resistance of the polymer solid-electrolyte compositions of the present invention are shown in Table 1 as follows:

TABLE 1

The water content and specific resistance of polymer solid electrolytes

| silica content (%) | water content (%) | specific resistance ($\Omega$ cm) at 80° C. |
| --- | --- | --- |
| 0.00 | 2.5 | 10.5 |
| 0.01 | 20.0 | 10.0 |
| 0.10 | 28.0 | 7.4 |
| 1.00 | 31.0 | 5.5 |
| 3.00 | — | 5.4 |
| 10.0 | 34.0 | 6.0 |
| 20.0 | — | 6.8 |
| 30.0 | — | 7.5 |
| 50.0 | — | 9.8 |

Note: These values in Table 1 were obtained by using fine particle silica but similar values were obtained by using fibrous silica fiber.

Note: These values in Table 1 were obtained by using fine particle silica but similar values were obtained by using fibrous silica fiber.

As clearly shown in the results in Table 1, the water content is 2.5% in the case where no silica was contained in the polymer solid electrolyte, whereas it is 20.0% even in the case where 0.01% of silica was added, the latter water content being about 10 times as much as the former. The specific resistance shows a minimum of 5.4 to a maximum of 10.0 $\Omega$ cm over the silica content range of 0.01–50.0%, and so the minimum has approximately twice the conductivity of the membrane without silica. Particularly, the membrane specific resistances were markedly decreased in the silica content range of 0.1–20%.

EXAMPLE 2

A preferred example in which the electrochemical cell using the polymer solid-electrolyte composition of the present invention is described, but the invention is not intended to be limited only to this following example.

Figure 1:
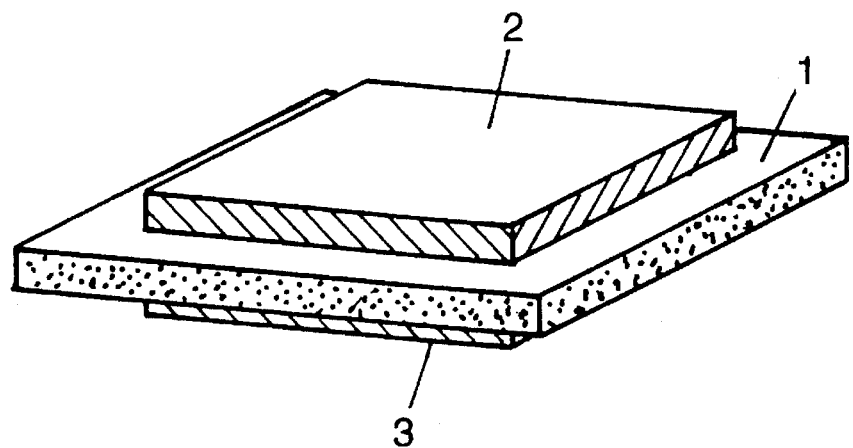
FIG. 1 is a perspective view of the polymer solid-electrolyte type of fuel cell in Example 2 as one example of the electrochemical cells.

FIG. 1 shows the polymer solid electrolyte type of fuel cell. Using this fuel cell, the ion-exchange membrane which forms polymer solid-electrolyte layer was prepared by the following preparation method.

First, a solution of 5% by weight of NAFION® in isopropanol (Aldrich) was mixed with a dispersion of 5% by weight of silica (e.g., Aerosil 380® under the trade name available from Nippon Aerosil Co., Ltd.; the mean primary particle size, 0.007 μm) in isopropanol (concentration: 5 g/l) and stirred with a ultrasonic homogenizer. Subsequently, the resulting solution was poured into a membrane-molding vessel and dried under a reduced pressure at 60° C. to remove the isopropanol so as to prepare an ion-exchange membrane, which has a silica content of 5% by weight and a membrane thickness of 0.1 mm. The membrane preparation also can be performed by an extrusion molding or screen process printing technique or any other membrane making process.

Then, the cathode catalyst layer and anode catalyst layer used in the fuel cell was prepared by the following method. First, the respective catalyst-solution in which platinum was dispersed on the surface of carbon particles, NAFION® and silica (1:1:0.05 in % by weight) in ethanol was well mixed with an ultrasonic homogenizer. After this solution was dried under a reduced pressure at 60° C. to remove the ethanol, the dried substance was crushed, and the resulting material was transferred to a carbon paper on the current collector electrode by the filtration-transfer method and hot-pressed under a pressure of 5 kg/cm² for 3 min at 130° C. to prepare a layer in the form of a thin sheet. The silica used was the same as in the preparation of the above-mentioned ion-exchange membrane. The silica content in the catalyst layer was 2.4% by weight relative to the weight of the catalyst layer. The cathode catalyst layer and the anode catalyst layer had the same silica content.

Figure 2:
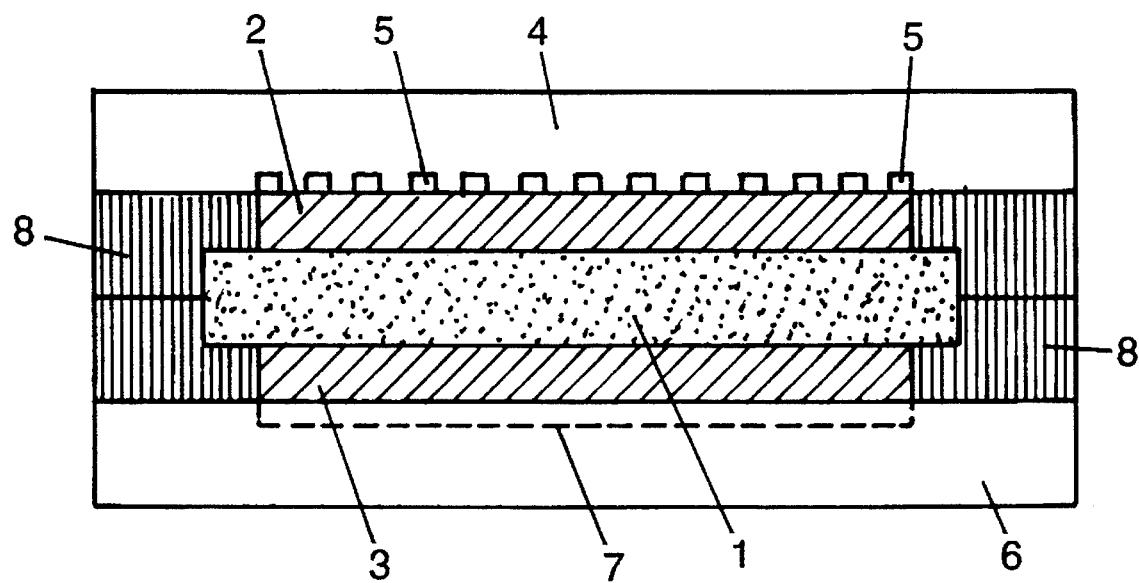
FIG. 2 is a sectional view of the polymer solid-electrolyte membrane type of fuel cell in Example 2 which is assembled into a single cell having a sealed structure.

Then, the ion-exchange membrane as prepared above was placed between the two catalyst electrodes as prepared above to assemble the polymer solid electrolyte type of fuel cell shown in FIGS. 1 and 2.

In FIGS. 1 and 2, the numeral 1 shows an ion-exchange membrane; the numeral 2 shows a cathode catalyst layer; the numeral 3 shows an anode catalyst layer; the numeral 4 shows a cathode current collector having oxygen feeder 5; the numeral 6 shows an anode current collector having hydrogen feeder 7; the numeral 8 shows a seal.

Further as a comparative example, a similar ion-exchange membrane, cathode catalyst layer, and anode catalyst layer were prepared except without silica, and the polymer solid-electrolyte type of fuel cell similar to that shown in FIG. 2 was assembled.

Figure 3:
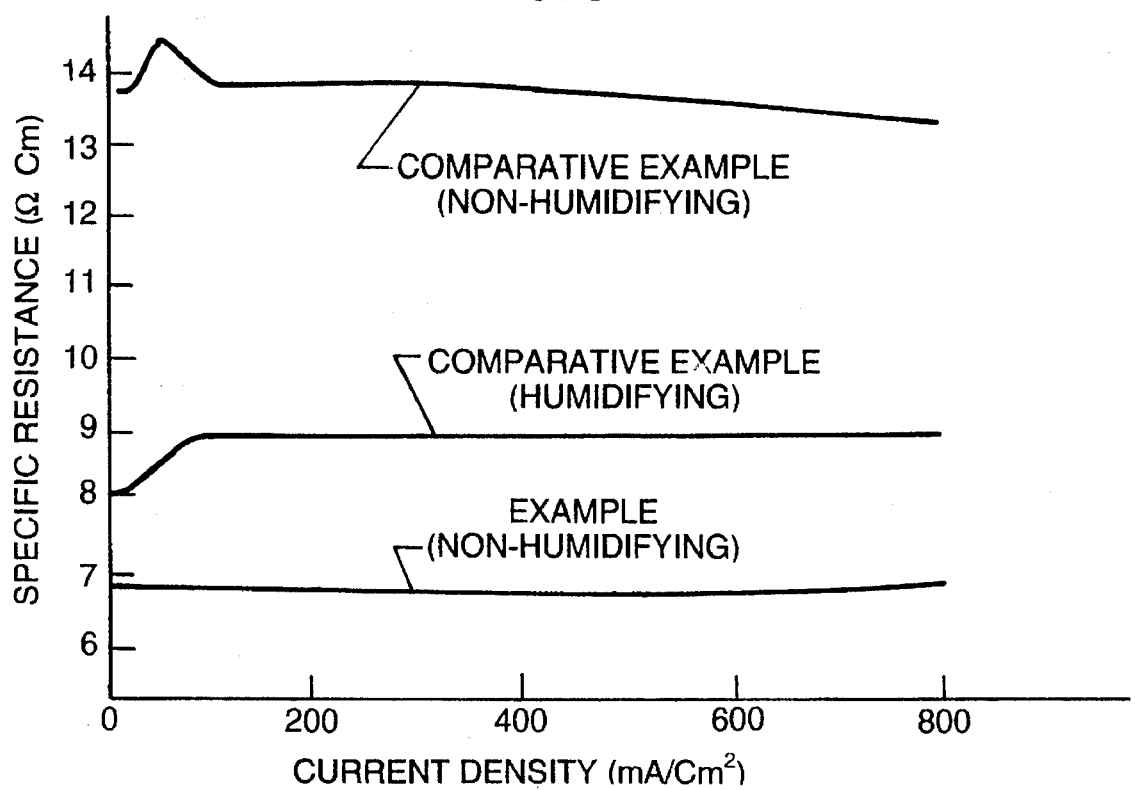
FIG. 3 is a graph in which the specific resistance of the polymer solid-electrolyte membrane type of fuel cell in Example 2 of the present invention is compared with that of the polymer solid-electrolyte membrane type of fuel cell in the Comparative Example.

The polymer solid-electrolyte type of fuel cell of the present invention, and the conventional, polymer solid-electrolyte type of fuel cell were evaluated for cell performance by the following comparative tests. 1) The polymer solid-electrolyte type of fuel cell was operated under non-humidifying conditions to measure the specific resistance. On the other hand, the polymer solid-electrolyte type of fuel cell prepared for the Comparative Example was operated under humidifying conditions with hydrogen gas and under non-humidifying conditions to measure the specific resistance. The operating conditions of these cells are as follows. The comparative results are shown in FIG. 3.

Reaction gas: hydrogen (the anode side) and oxygen (the cathode side)

Cell-operating temperature: 80° C.

Humidifying temperature: 80° C.

Cell-operating pressure: atmospheric pressure

As clearly shown in the results in FIG. 3, the specific resistance of the polymer solid-electrolyte/silica fuel cell of this Example in the present invention even under non-humidifying was less than that of the polymer solid-electrolyte without silica fuel cell of the Comparative Example, which showed improved ion conductivity for the former cell. This also showed comparatively high specific resistance for the latter cell.

These results have showed that the cell performance of the polymer solid-electrolyte/silica fuel cell according to the present invention even under non-humidifying conditions was better than that of the polymer solid-electrolyte type of fuel cell of the Comparative Example. 2) When both of the polymer solid-electrolyte type of fuel cell of the present invention and the conventional, polymer solid-electrolyte type of fuel cell were operated under non-humidifying conditions at a current density of 350 mA/cm², then constancy of cell voltage for both cells were compared. The results are shown in FIG. 4.

Figure 4:
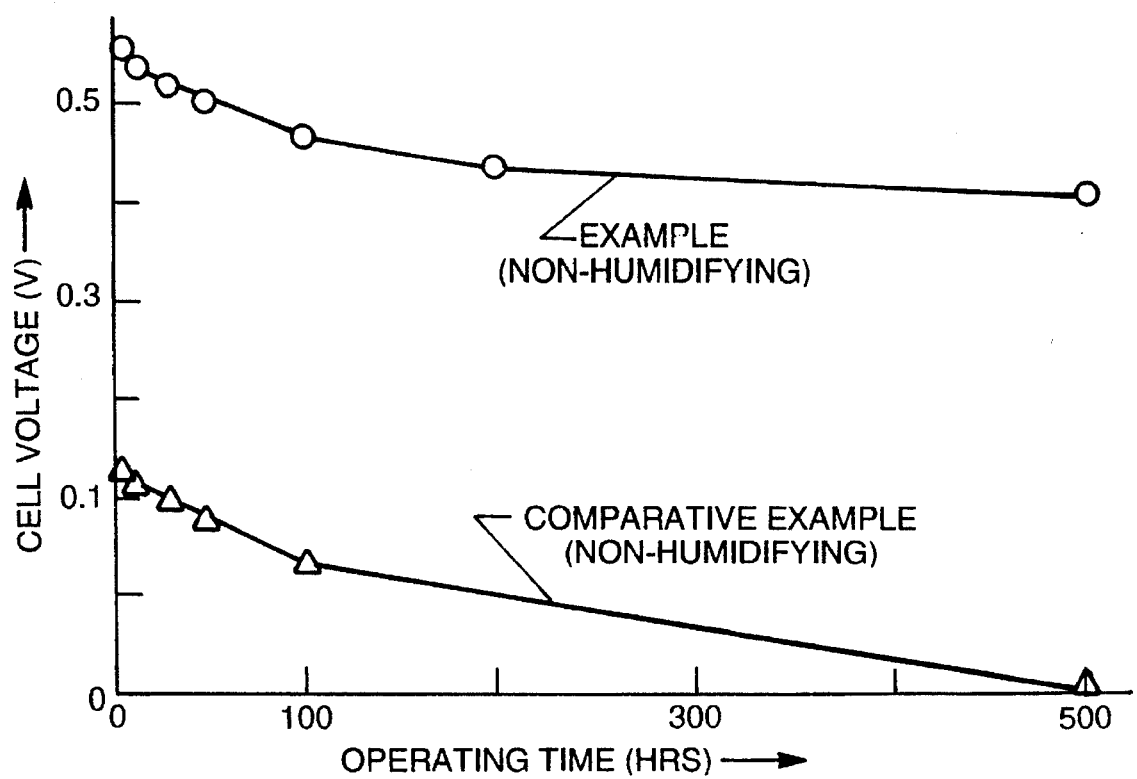
FIG. 4 is a graph in which the cell's life of the polymer solid-electrolyte membrane type of fuel cell in Example 2 of the present invention is compared with that of the polymer solid-electrolyte membrane type of fuel cell in the Comparative Example.

As shown from the results in FIG. 4, it was clear that the cell performance of the polymer solid-electrolyte/silica fuel cell according to the present invention was higher than that of the polymer solid-electrolyte without silica fuel cell of the Comparative Example. Further, the polymer solid-electrolyte type of fuel cell according to the present invention even under non-humidifying conditions has maintained stable cell performance for as long as 500 hours.

These results were able to confirm that the polymer solid-electrolyte/silica fuel cell according to the present invention allows non-humidifying operation.

EXAMPLE 3

The fine particle silica was used to prepare the ion-exchange membrane in Example 2; whereas in Example 3 an ion-exchange membrane was prepared which contained 5% by weight of silica short fiber with a diameter of 3 μm relative to the weight of NAFION® by the similar method of membrane preparation to the method in Example 2 so as to produce a polymer solid-electrolyte membrane type of fuel cell. The polymer solid-electrolyte membrane type of fuel cell had the same structure as that in Example 2 except for the ion-exchange membrane. This polymer solid-electrolyte membrane type of fuel cell was determined for the specific resistance under the non-humidifying operation or under the humidifying operation. As a result, the specific resistance under non-humidifying operation was 7 Ω cm, and the same value was obtained in the case where the silica fiber was contained. On the other hand, the specific resistance under humidifying operation was a smaller value, i.e., 5 Ω cm.

EXAMPLE 4

Figure 5:
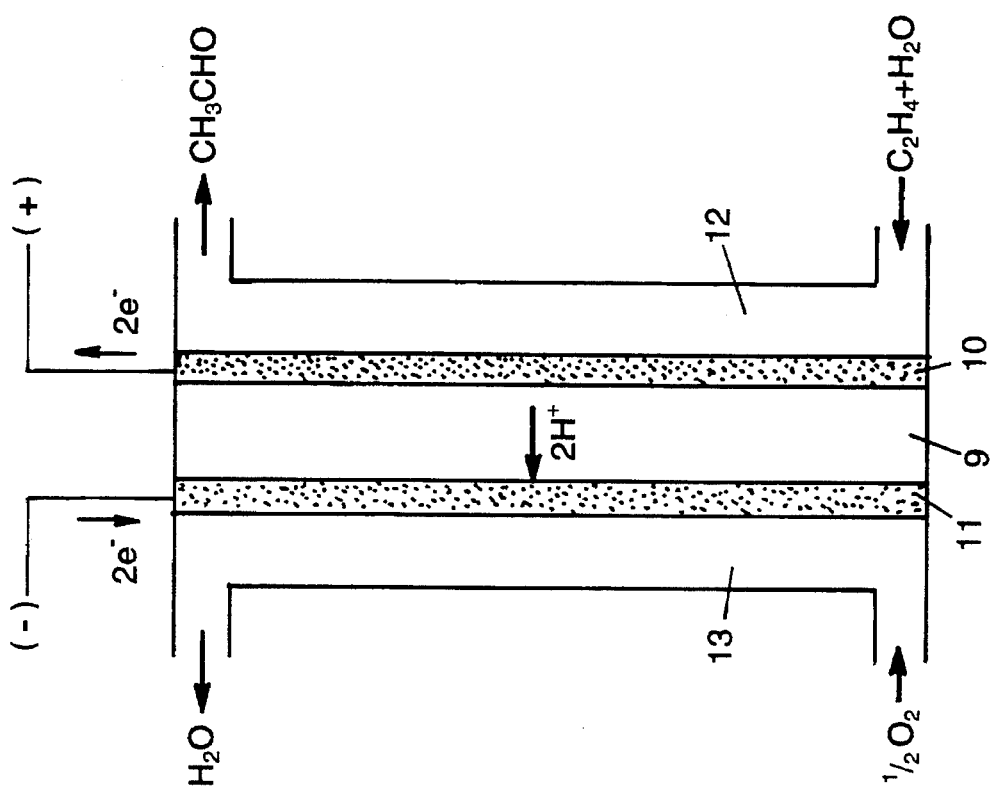
FIG. 5 is a structure view of the ion-exchange membrane type of ethylene-partially oxdative acetaldehyde-synthesis cell in Example 3 as one example of the electrochemical cell.

Another Example of an electrochemical cell according to the present invention will be illustrated as follows:

FIG. 5 shows an ion-exchange membrane type of acetaldehyde synthesis cell. The numeral 9 indicates the ion-exchange membrane; the numeral 10 indicates a porous anode of palladium catalyst; the numeral 11 indicates a porous cathode of palladium catalyst; the numeral 12 indicates the ethylene feeder; the numeral 13 indicates the oxygen gas feeder. Then, a membrane having a thickness of 0.15 mm was prepared with the polymer solid-electrolyte composition of the present invention (containing 5% by weight of silica in NAFION®) was used as an ion-exchange membrane. Further, as Comparative Example an ion-exchange membrane type of acetaldehyde-synthesis cell was prepared using an ion-exchange membrane of NAFION® without silica.

As a result, the specific resistance of the ion-exchange membrane type of acetaldehyde-synthesis cell using the polymer solid-electrolyte composition of the present invention as an ion-exchange membrane was about half of the Comparative Example. Thus, since the transfer rate of hydrogen ions was improved, hydrogen ions and oxygen gas caused an effective electrode reaction at the porous cathode, and the production of acetaldehyde due to the partial oxidation of ethylene was found to increase.

In addition, since the excess water generated at the porous cathode of palladium catalyst diffuses to the side of the ion-exchange membrane, it was also found that the water did not inhibit diffusion of oxygen gas to the porous cathode.

EXAMPLE 5

Figure 6:
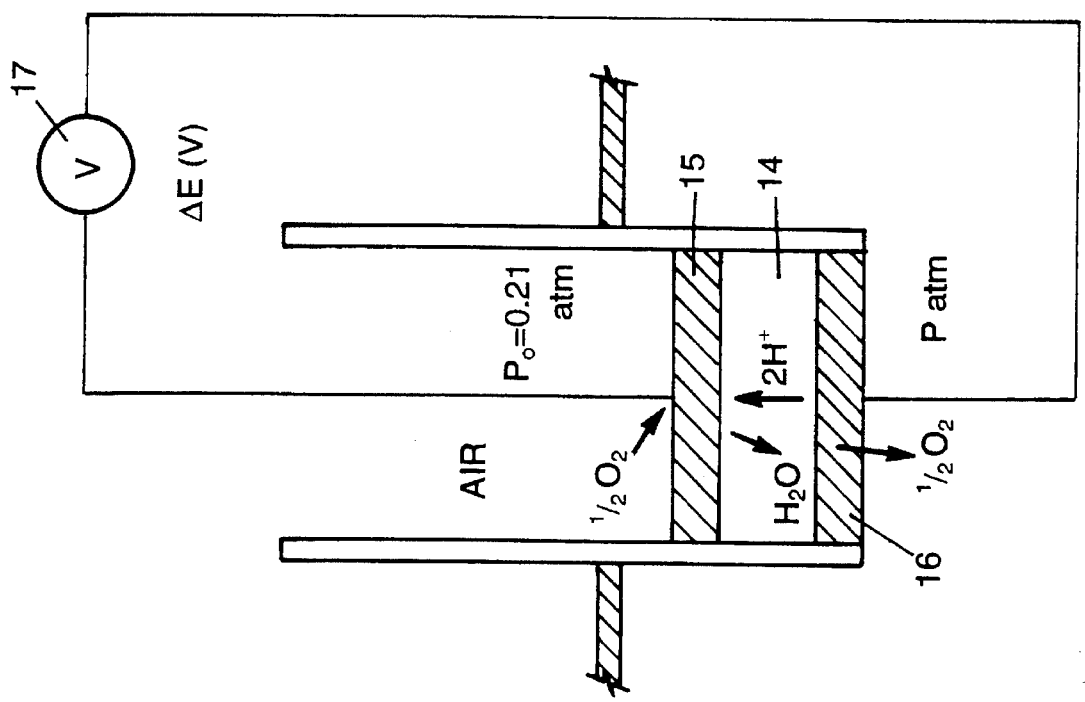
FIG. 6 is a structure view of the ion-exchange membrane type of oxygen sensor in Example 4 as one example of the electrochemical cell.

Another example of the electrochemical cell of the present invention will be illustrated as follows:

FIG. 6 shows an ion-exchange membrane type of oxygen sensor. The numeral 14 indicates the ion-exchange membrane; the numeral 15 shows one side of porous electrodes of platinum catalyst; the numeral 16 shows another side of porous electrodes of platinum catalyst;

and the numeral 17 shows the static charge gauge, which measures oxygen concentrations according to the potential difference between both electrodes. On the other hand, as Comparative Example an ion-exchange membrane type of oxygen sensor was prepared using an ion-exchange membrane of NAFION® without silica.

As a result, without making the ion-exchange membrane type of oxygen sensor of the Comparative Example contain water, the performance decreased. On the contrary, the ion-exchange membrane type of oxygen sensor prepared with the polymer solid-electrolyte/silica composition of the present invention as an ion-exchange membrane had sufficient moisture absorption to decrease the humidity.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A polymer solid-electrolyte composition comprising a resin selected from the group consisting of cationic-exchange resins and anionic-exchange resins, wherein the cationic-exchange resin is selected from the group consisting of perfluorocarbon sulfonic acids, polysulfones, perfluorocarbonic acid and styrene-divinylbenzene sulfonic acid, said resin containing a silica dispersed therein in an amount of 0.01–50 wt. %, based on the weight of the composition, and said silica is selected from the group consisting of particulate silicas having a mean primary particle size of 0.1 µm or less and fibrous silicas having a diameter of 6 µm or less.

2. The composition of claim 1, wherein the anionic-exchange resin is a styrene-butadiene resin.

3. An electrochemical cell consisting of an anode, a layer of a polymer solid-electrolyte composition and a cathode, said composition comprising a resin selected from the group consisting of cationic-exchange resins and anionic-exchange resins, wherein the cationic-exchange resin is selected from the group consisting of perfluorocarbon sulfonic acids, polysulfones, perfluorocarbonic acid and styrene-divinylbenzene sulfonic acid, said resin containing a silica dispersed therein in an amount of 0.01–50 wt. %, based on the weight of the composition, and said silica is selected from the group consisting of particulate silicas having a mean primary particle size of 0.1 µm or less and fibrous silicas having a diameter of 6 µm or less and said composition is used as at least one of said electrolyte in said anode and/or said cathode, or said layer.

4. The electrochemical cell of claim 3 wherein the anionic-exchange resin is a styrene-butadiene resin.

5. A fuel cell having a cathode current collector, a cathode catalyst layer, a layer of a polymer solid-electrolyte composition, an anode catalyst layer and an anode current collector laminate, said catalyst layer supplied with an oxidative gas and anode catalyst layer supplied with a fuel gas, said composition comprising a resin selected from the group consisting of cationic-exchange resins and anionic-exchange resins, wherein the cationic-exchange resin is selected from the group consisting of perfluorocarbon sulfonic acids, polysulfones, perfluorocarbonic acid and styrene-divinylbenzene sulfonic acid, said resin containing a silica dispersed therein in an amount of 0.01–50 wt. %, based on the weight of the composition, and said silica is selected from the group consisting of particulate silicas having a mean primary particle size of 0.1 µm or less and fibrous silicas having a diameter of 6 µm or less, wherein at least one of said cathode catalyst layer, layer of polymer solid-electrolyte composition and anode catalyst layer comprises said silica.

6. The fuel cell of claim 5 wherein the anionic-exchange resin is a styrene-butadiene resin.

\* \* \* \* \*